United States Patent [19]

L'Esperance, Jr.

[11] Patent Number: 4,538,608

[45] Date of Patent: Sep. 3, 1985

[54] METHOD AND APPARATUS FOR REMOVING CATARACTOUS LENS TISSUE BY LASER RADIATION

[76] Inventor: Francis A. L'Esperance, Jr., 255 Oakwood Rd., Englewood, N.J. 07631

[21] Appl. No.: 617,931

[22] Filed: Jun. 6, 1984

Related U.S. Application Data

[63] Continuation-in-part of Ser. No. 592,710, Mar. 23, 1984, and a continuation-in-part of Ser. No. 592,709, Mar. 23, 1984, said Ser. No. 592,710, Continuation-in-part of Ser. No. 571,827.

[51] Int. Cl.$^3$ .............................................. A61B 17/36
[52] U.S. Cl. .................................. 128/303.1; 128/395; 364/413; 364/525; 372/24
[58] Field of Search ............... 128/303.1, 395; 372/24; 364/413, 525

[56] References Cited

U.S. PATENT DOCUMENTS

| | | | |
|---|---|---|---|
| 3,653,384 | 4/1972 | Swope | 372/15 |
| 3,720,213 | 3/1973 | Hobart et al. | 128/303.1 |
| 3,783,874 | 1/1974 | Koester et al. | 128/303.1 |
| 3,828,788 | 8/1974 | Krasnov et al. | 128/303.1 |
| 3,971,382 | 7/1976 | Krasnov | 128/303.1 |
| 3,992,682 | 11/1976 | White et al. | 372/24 |
| 4,024,866 | 5/1977 | Wallach | 364/413 |
| 4,091,814 | 5/1978 | Togo | 128/303.1 |
| 4,309,998 | 1/1982 | Aron nee Rosa et al. | 128/303.1 |
| 4,391,275 | 7/1983 | Fankhauser et al. | 128/303.1 |
| 4,477,905 | 10/1984 | Sweeney | 372/30 |

FOREIGN PATENT DOCUMENTS

WO80/00480-06  6/1980  PCT Int'l Appl. .......... 128/303.1

OTHER PUBLICATIONS

Taboada et al., "Response of the Corneal Epithelium to KrF Excimer Laser Pulses", Health Physics, v. 40 (May), pp. 677–683, 1981.

Primary Examiner—D. E. Gantz
Assistant Examiner—Lance Johnson
Attorney, Agent, or Firm—Hopgood, Calimafde, Kalil, Blaustein & Judlowe

[57] ABSTRACT

The invention involves the apparatus and the technique for non-invasive surgery to remove cataracted-lens tissue from an afflicted lens. The beam output of a laser is focused to a spot of maximum power density at the anterior surface of a cataracted lens and scanned over a predetermined area or areas of the cataracted lens. The beam is selective and safe since it's diffuse as it enters the eye through the cornea and is also diffuse (being divergent) in the unlikely event that the beam passes through an opening it has created in the cataracted lens. This diffusion assures against damage to either or both of the cornea and the retina. Focal power levels are used sufficient to achieve cataract material destruction thru ablative photodecomposition, thermal decomposition, photofragmentation, photoemulsification or any combination thereof. Various features are disclosed for assuring safety and uniformity in the removal of involved tissue.

23 Claims, 3 Drawing Figures

METHOD AND APPARATUS FOR REMOVING CATARACTOUS LENS TISSUE BY LASER RADIATION

BACKGROUND OF THE INVENTION

This application is a continuation-in-part of my application Ser. No. 592,710 and Ser. No. 592,709, both filed Mar. 23, 1984, and said application Ser. No. 592,710 is a continuation-in-part of my application Ser. No. 571,827, filed Jan. 19, 1984.

The invention relates to laser surgery and in particular to a method and apparatus for non-invasively removing cataractous lens tissue from an afflicted eye.

Present-day methods for removing cataractous tissues or cataracts are surgically invasive and relatively complicated, requiring the use of a hospital operating room, sterile conditions, sutures, and other instrumentation. Furthermore, recovery from such an operation involves a relatively long rehabilitation period and other complications attendant with invasive surgery.

Accordingly, it is desirable to carry out such operations using surgically non-invasive or relatively non-invasive techniques. Such non-invasive techniques would allow a doctor to conduct cataract-removal procedures on an out-patient basis, eliminating the expense and complications attendant with invasive surgery.

The search has continued for new methods of removing cataracts via a simple procedure which may be conducted on an out-patient basis. The present invention has been made as a result of that search.

BRIEF STATEMENT OF THE INVENTION

It is a general object of the invention to avoid or substantially eliminate above-identified problems of the prior art.

Another object is to provide a method and apparatus for non-invasive removal of cataractous natural-lens tissue from an afflicted eye.

A specific object is to meet the above objects without damage to the retina or to the cornea.

A further specific object is to provide the ophthalmological surgeon with a tool for performing a cataract-removal operation of the character indicated, with minimum dependence upon the manipulative skill of the surgeon.

The invention meets these objectives and provides certain further features in apparatus (a) which enables the beam output of a laser to be focused from a convergent-ray bundle to a focal spot of maximum power density at the anterior surface of a cataracted lens and (b) which scans the focal spot over a predetermined area or areas of the cataracted lens. The beam is afocal and therefore diffuse as it enters the eye through the cornea, and it is also diffuse (being divergent) in the controllably unlikely event that the laser energy passes through an opening it has created in the cataracted lens; the diffusion assures against damage to either or both of the cornea and the retina, for power levels sufficient to achieve ablative photodecomposition and/or thermal decomposition and/or photofragmentation and/or photoemulsification of the cataracted-lens tissue. Various features are disclosed for assuring safety and uniformity in the removal of involved tissue.

DETAILED DESCRIPTION

The invention will be illustratively described in conjunction with the accompanying drawings, in which.

Figure 1:
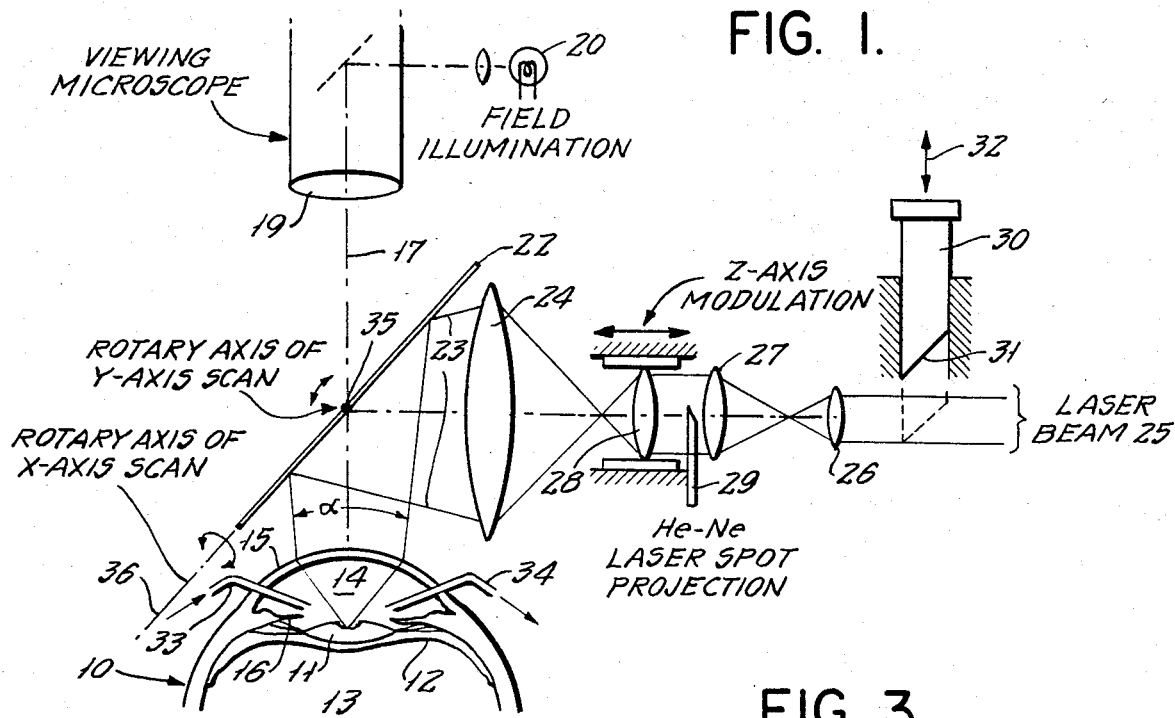
FIG. 1 is a simplified optical diagram of components of apparatus of the invention, shown in application to an eye in which cataracted-lens tissue is being removed.

In FIG. 1, a patient's eye 10 is shown with a cataracted natural lens 11 which will be understood to be confined by a posterior capsule or sac (not shown). The vitreous membrane 12 separates the vitreous body 13 from aqueous contents, primarily in the anterior chamber 14, the confined by the cornea 15 and including a dilated iris 16, dilation being to establish an opening of 7 to 8 mm diameter about the central axis 17 of the eye. The patient's head will be understood to have been immobilized by suitably fixed restraint (not shown), and anesthesia and akinesia of the lids and extraocular muscles will be understood to have been created by a lid-anesthetic block and retrobulbar injection of local anesthetic solution (e.g., Xylocaine 2%).

The objective lens 19 of a viewing microscope is shown to have been aligned with the axis 17. The microscope may be of the binocular-viewing stereo variety, including a local light source 20 and suitable optical means for projecting visible light through objective 19 for illumination of the field of view of non-invasive surgery on lens 11. The term "Viewing Microscope" will be understood to be a generic designation of purely optical means (such as the binocular device mentioned above) as well as electronically scanned means (such as a video camera, equipped with objective 19).

Field viewing via objective 19 is through a partially reflecting mirror 22 which also serves to fold the bundle of rays 23 shown issuing from a fixed objective 24 and convergent at an included angle α to the surface of the cornea 15, beyond which the rays are further convergent to a focal spot at the cataracted lens 11. The ray bundle 23 is largely comprised of laser energy from a suitable source (not shown) but having an output beam 25 which is subjected to expansion via a first pair of optical elements 26-27, and then via a second pair which includes the objective 24 and another element 28. Element 27 establishes a collimated-light region between elements 27-28, and element 28 is mounted for axial displacement, to permit Z-axis manipulation (or modulation) of the depth position of the focal spot of greatest laser-power density within the cataracted lens 11. Means such as a helium-neon laser is suggested by legend as providing a steady source of visible light via a rod or fiber element 29 having a truncated end for projecting visible light through the focusing system of lenses 28-24, so that the spot of instantaneous laser-energy focus can also be a visible spot in the field of view of the microscope. Finally, a shutter comprising a transversely actuable body 30 with a sloped reflecting end face 31 is actuable into and out of laser beam 25 for transient effective discard of laser output, when necessary or desired, all as suggested by a double-headed arrow 32.

The laser which produces the beam 25 may be a commercially available near-infrared pulsed laser of the neodymium-YAG variety wherein the energy of individual pulses is from about 1 to about 30 millijoules, in which case the preferred convergent-ray angle $\alpha$ is in the range of about 16 to about 20 degrees. In this event, the focal spot of laser energy induces photofragmentation and/or photoemulsification of cataractous tissue of lens 11. Alternatively and preferably, the laser beam 25 may be the output of an ultraviolet laser, such as an excimer laser or a frequency-quadrupled neodymium-YAG laser, producing a focal spot which decomposes the cataractous tissue of lens 11 through ablative photodecomposition and/or thermal decomposition, depending upon the wavelength of involved laser radiation; in the excimer-laser situation, the convergence angle $\alpha$ is preferably in the range from about 25 to about 30 degrees, the power density at the focal spot is about 1 to about 5 joules per square centimeter, and the diameter of the focal spot is in the range from about 30 to about 100 microns. The depth of ablation for each excimer-laser pulse is about 1 to 2 microns, and the frequency of pulse repetition is in the range from about 20 to about 500 pulses per second.

Whatever the laser selected for use of the invention, it will be understood that power levels are selected to achieve the indicated decomposition at the focal spot but to be sufficiently diffuse at entry to the cornea and, in the event of passage to the retina, to be of no harm to either the cornea or the retina. Also, the indicated decomposition of cataractous-lens tissue is not without generation of bubbles and/or fragmented debris within the aqueous of anterior chamber 14, and an irrigation-/aspiration procedure is recommended to remove the same. Such procedure may involve a single canula device as described in said application Ser. No. 592,710, or, as shown, a first needle probe 33 through the cornea at one margin location may discharge a flow of isotonic purging solution into the anterior chamber 14 while another such probe 34 draws off a corresponding flow.

The mirror 22 is a component part of a two-dimensional scanning system for causing the focal spot (at lens 11) to sweep a regular pattern of coverage of the field (i.e., of lens 11) which is to be surgically non-invasively decomposed by laser action. The swept field is thus generally transverse or normal to the axis 17 and is also therefore generally normal to the Z-axis displacement capability of the focal spot by reason of axial displacement of optical element 28. The swept field may be covered by any of a variety of known mirror-displacement techniques, utilizing polar-coordinates (where radius R and angular displacement $\theta$ are the variables), or utilizing rectilinear coordinates (where horizontal displacement X and vertical displacement Y are the variables). For diagrammatic and descriptive purposes, it is more simple to consider mirror 22 as being mounted via a two-axis gimbal system, wherein a first pivot axis 35 (perpendicular to the plane of FIG. 1) is the reference about which mirror 22 is reciprocably tilted to produce a Y-axis component of focal-spot displacement, and wherein a second pivot axis 36 (in the plane of FIG. 1) is the reference about which mirror 22 is reciprocably tilted to produce an X-axis component of focal-spot displacement.

Figure 2:
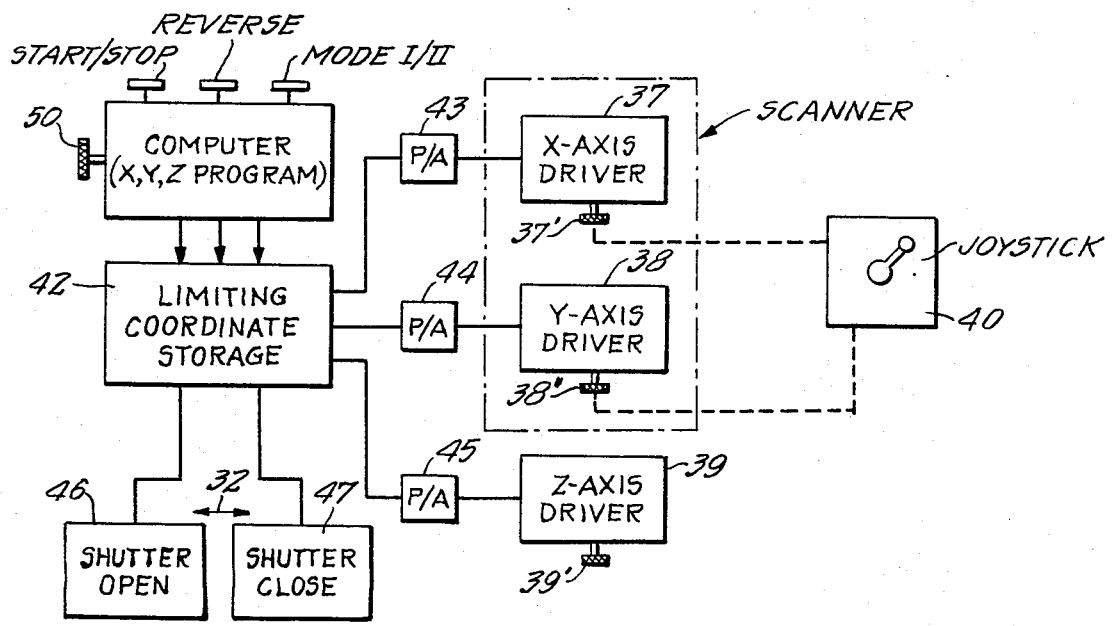
FIG. 2 is a simplified block diagram of computer and scanner control elements used in connection with the apparatus of FIG. 1.

Referring now to FIG. 2, separate drive systems or actuators 37-38-39 are shown for imparting displacement motion to each of the respective X, Y and Z-axis components of scanning and depth motion of the focal spot. The X-axis and Y-axis drivers 37-38 impart rotary reciprocation about axes 36-35 in a coordinated pattern to develop a raster-like scan of the field, and the Z-axis driver 39 imparts linear reciprocation along the involved part of the axis of laser projection (including visible light projection from means 29). Drivers 37-38-39 may be servo motors responding to analog inputs. In a first mode (shown by legend to be selected at a computer 41), each of the drivers is manually operated, as suggested by associated knobs 37'-38'-39'; and for purposes of coordinated positioning of the focal spot in the scanable X-Y field, a single joystick control 40 is shown with connections to the first-mode inputs 37'-38' of the X-Y field. In a second mode, computer 41 is programmed for a predetermined coordination of X-Y-Z component displacement to accomplish X-Y scanning as a function of depth (Z-axis) scanning, all within a predetermined volume of stored digital data at means 42, for outer limits of scan action. Digital/analog devices 42-43-44 couple the three limited-coordinate outputs of means 42, to the respective drivers 37-38-39, for second-mode operation. Separate outputs 46-47 are also shown for the shutter-open and shutter-close action suggested by the double-headed arrow 32 of FIG. 1.

An illustrative technique of use of the described apparatus will now be given, commencing after the fixation, blocking and anesthetizing procedures have been accomplished:

1. The surgeon maintains continuous monitoring vigil of the field (lens 11), as viewed and illuminated via objective 19.

2. He then initiates visible-light projection of the focal spot (of system 28-24) via injection means 29.

3. He positions the focal spot on lens 11 at a point on the outer perimeter which he elects to define as an outer limit of surgery, adjustment being manual at 40 and at 39'.

4. Once satisfied as to focus on the elected outer perimeter, the operator activates means 42 to enter into storage the two-dimensional focal-spot coordinates (X-Y).

5. Joystick 40 is then manipulated to move the visible spot in a continuous circular path which is to become the limiting perimeter of lens-tissue decomposition; in the event of video observation via objective 19, it will be understood that an associated field-monitoring display (not shown) may include means for continuous display of the perimeter thus described by joystick manipulation and entered into storage at 42.

Figure 3:
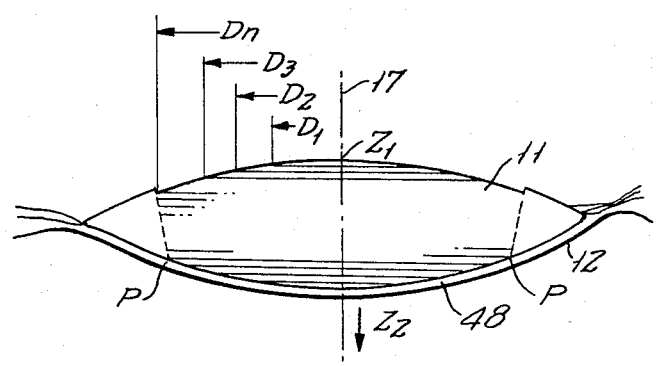
FIG. 3 is a diagram on an enlarged scale to illustrate a program of scan action, involved in use of the apparatus of FIGS. 1 and 2.

6. All is now in readiness for commencement of non-invasive laser surgery, subject to:

(a) centering the joystick position (focal spot on axis 17) and making a Z-axis adjustment at 39' to assure focus at the anterior surface of lens 11 for this centered position;

(b) entering into storage a first circular perimeter of relatively small diameter $D_1$ to limit X-Y scan at the central focus setting $Z_1$ (see FIG. 3); and (c) entering into storage a succession of increased diameters $D_2$, $D_3$ . . . $D_n$ determining progressively expanding limits of X-Y scan at each of a succession of X-Y scans, it being understood that diameter $D_n$ corresponds to the stored outer limiting perimeter described in connection with step 5 above, and it being further understood that for each of these successive diameters, a corrective Z-axis increment of indexed drive is entered into storage, consistent with the known Z-axis or depth dimension of laser-pulse ablation or other decomposition of lens tissue, whereby each X-Y scan of its particularly limited field can be at a correct Z-axis focal-spot position of depth in lens 11.

7. Visible-light display of the circle of the limiting perimeter described in connection with step 5 above is no longer necessary, so that the source for light injected at 29 may be switched off, with reliance only upon stored memory of its coordinate data. At the same time, the isotonic injection/aspiration flow via 33–34 is initiated.

8. The laser beam 25 is activated and shutter 30 activated to expose laser radiation to lens 11 in accordance with computer control of X, Y, Z action (start/stop button at computer 41), as limited by stored perimeter coordinates for each of the succession of scans, thus effectively shaving by layer decomposition, up to the nth layer, at which point the stored outer limiting perimeter will have been reached.

9. The surgeon continues the X-Y scans at full or substantially full perimeter (diameter $D_n$ for a sequence of successive Z-axis increments), until his observation of the field reveals a perceptible reddening color change of the outer perimeter (due to light reflected from posterior-eye structure). This color change signals that the surgery has progressed to a depth at which all or substantially all cataracted tissue has been removed at the perimeter (designated P in FIG. 3).

10. Once the disclosed perimeter P is observed, a "Reverse" button is pressed at computer 41 to initiate a reversed succession of limiting-perimeter X-Y scans (at diameters, $D_{n-1}, D_{n-2} \ldots D_1$) for successive Z-axis or depth increments. Observation of the field should show progressively inward spreading of an annulus of color change which is indicative of accomplished decomposition of cataractous tissue, until the last X-Y scan, within the minimum limiting perimeter of diameter $D_1$, whereupon shutter 30 will have been actuated to closed position and/or laser beam 25 shutdown, all under computer control.

11. The described sequence of operations will be understood to enable and involve a fully automatic "rough cut" in which all or substantially all cataractous-lens tissue will have been removed, with possible partial removal of posterior-capsule tissue (at layer 48 in FIG. 3). At the same time, careful inspection under microscope may reveal isolated local regions of remnant cataractous tissue. The "fine cut" removal of such remnant tissue may be accomplished by manual (e.g., joystick 40) maneuvering of a small-perimeter region within the field, at a reduced level of laser-beam energy, all while observing uniformly reddened color change of the field. Alternatively, areas to be fine-cut vs. areas not to be fine-cut may be defined by closed-perimeter development through joystick manipulation of the spot of focused light, with concurrent coordinate-data entry into storage, and one or more single X-Y scans at the adjusted appropriate depth of Z-axis depth may be automatically run via computer control, as limited by the stored coordinate-data of the involved closed perimeter or perimeters, circular or otherwise shaped. The described invention will be seen to have achieved all stated objects, with a basic simplicity of operation, in that the customary finely tuned manual skill and dexterity of the ophthalmological surgeon is no longer required. Partial removal of posterior-capsule tissue is of no significance since it is not characterized by the light-attenuating or light-diffusing or scattering properties of cataractous tissue, and no substantial harm flows from an inadvertent failure to remove all the cataractous tissue. The main point is that the invention permits removal of all the cataractous tissue, as long as the surgeon or operator is careful to recognize that it remains to be removed, however local the remnant.

While the invention has been described in detail for preferred apparatus and technique, it will be understood that modifications may be made without departing from the scope of the invention. For example, a simple provision for manual adjustment (suggested at 50 in FIG. 2) of the computer program can enable the operator/surgeon to change the rate of limiting perimeter increment and/or decrement as may be judged more appropriate for accommodating X-Y scan limitations, from one to the next scan, to the particular lens (11) curvatures which the skilled surgeon can perceive in his viewing of each patient's particular lens (11) contour configuration.

What is claimed is:

1. Apparatus for surgical, non-invasive destruction of cataracted natural-lens tissue within an afflicted eye, comprising viewing means having an optical objective on a viewing axis adapted for alignment with the afflicted eye, a laser and optical means for treating the beam output of said laser to translate said output into a conical ray bundle convergent to a focal spot of maximum power density, said optical means including an axially movable element for providing Z-axis displacement of said focal spot, a visible-light source and means including at least said movable element for translating visible-light output of said source into at least part of the conical-ray bundle convergent to said focal spot, two-component scanning means interposed in said convergent-ray bundle for scan deflection of said focal spot in directions normal to the Z-axis, said scanning means and said optical means being so positioned as to place said focal spot at the cataracted lens with the viewing axis normal to the center of the field of two-component scan, said scanning means being adapted in a first selected mode for selective manipulation of displacement in each of the two component actions thereof, and said scanning means being adapted in a second selected mode for automated scan displacement of said focal spot under computer control and within said field, whereby in said first mode and using the visible-light output of said source, said focal spot may be selectively and adjustably progressed in a visually observed path of displacement to develop a closed perimeter of desired limiting laser action on the cataracted lens, computer means including a data-storage device and means for entering therein coordinate data for the observed development of said closed perimeter, said computer means including a program for control of the component actions of said scanning means as limited by said closed-perimeter data, and variable means associated with said computer means for effecting predetermined shrinkage of the field area of programmed scanning, within said closed perimeter and as a function of Z-axis displacement of said focal spot.

2. Apparatus according to claim 1, in which said two-component scanning means is of the orthogonally related X-Y variety.

3. Apparatus according to claim 1, in which said two-component scanning means is of the polar R-θ variety.

4. Apparatus according to claim 1, in which said variable means is computer controlled for initial scan of a predetermined most-reduced central area within said perimeter for a first Z-axis position selected to place said focal spot at the anterior surface of the cataracted lens, and in which said variable means is computer controlled for a subsequent scan of a less-reduced central area within said perimeter for a subsequent Z-axis position selected to place said focal spot at a posteriorly indexed position within the cataracted lens.

5. Apparatus according to claim 1, in which said viewing means is a stereo microscope.

6. Apparatus according to claim 5, in which said microscope includes a local light source and optical means for illuminating the field of scanning with light from said local source.

7. Apparatus according to claim 1, in which said variable means includes selectively variable means for adjustably positioning, within said closed perimeter, a shrunken field area of programmed scanning, whereby as an operator notes by local color change that cataracted lens tissue has been removed at least to the depth of the posterior capsule, said operator may reduce and shift the scanned local region to avoid further laser action at the region of local color change.

8. Apparatus according to claim 1, in which said computer means further includes means for entering in said data-storage device the coordinate data for the observed development of a second and more locally closed perimeter defined by an operator who has noted by local color change that cataracted lens tissue has been removed at least to the depth of the posterior capsule, the more locally closed perimeter being as developed by observation of the focal spot of visible light in a first-mode operation of said scanning means following a period of laser operation and second-mode scanning, said computer means being programmed for two-dimensional scan action without incursion into the area of said second and more locally closed perimeter.

9. Apparatus according to claim 8, in which a shutter is included in the beam output of said laser and in which said shutter is computer-controlled to preclude laser-output focus at the focal spot during periods of scanner deflection of the spot through the more locally enclosed perimeter.

10. The apparatus according to claim 1, in which the laser is pulsed laser wherein the energy of individual pulses is from about 1 to about 30 millijoules.

11. The apparatus according to claim 10, in which the convergent ray bundle has an included angle in the range of about 16 to about 20 degrees at entrance to the cornea of the eye.

12. The apparatus according to claim 10, in which the laser is of the neodymium-YAG variety.

13. The apparatus according to claim 1, in which the laser is of a variety characterized by emission in the ultraviolet.

14. The apparatus according to claim 1, in which the laser is an excimer laser.

15. Apparatus for surgical, non-invasive destruction of cataracted natural-lens tissue within an afflicted eye, comprising
viewing means having an optical objective on a viewing axis adapted for alignment with the afflicted eye,
a laser and optical means for treating the beam output of said laser to translate said output into a conical ray bundle convergent to a focal spot of maximum power density, said optical means including an axially movable element for providing Z-axis displacement of said focal spot,
a visible-light source and means including at least said movable element for translating visible-light output of said source into at least part of the conical-ray bundle convergent to said focal spot,
two-component scanning means interposed in said convergent-ray bundle for scan deflection of said focal spot in directions normal to the X-axis, said scanning means and said optical means being so positioned as to place said focal spot at the cataracted lens with the viewing axis normal to the center of the field of two-component scan, said scanning means being adapted in a first selected mode for selective manipulation of displacement in each of the two component actions thereof, and said scanning means being adapted in a second selected mode for automated scan displacement of said focal spot under computer control and within said field,
whereby in said first mode and using the visible-light output of said source, said focal spot may be selectively and adjustably progressed in a visually observed path of displacement to develop a closed perimeter of desired limiting laser action on the cataracted lens,
computer means including a data-storage device and means for entering therein coordinate data for the observed development of said closed perimeter, said computer means including a program for control of the component actions of said scanning means as limited by said closed-perimeter data, and
selectively variable means associated with said computer means for selectively and differently limiting the field area of programmed scanning, within said closed perimeter, for each of a plurality of Z-axis displaced positions of said focal spot.

16. A method of surgical, non-invasive destruction of cataracted natural lens tissue within an afflicted eye, said method comprising
(a) optically treating the beam output of a laser such that said beam output is translated into a conically convergent ray bundle to a focal spot of maximum power density,
(b) orienting said ray bundle to focus on said lens tissue via transmission through the cornea of the eye, whereby said maximum power density is focused at the lens tissue but the cornea and retina of the eye are exposed to relatively diffused and substantially reduced power density,
(c) exciting the laser to induce ablative photodecomposition and/or thermal decomposition and/or photofragmentation and/or photoemulsification via said maximum power density but at a level such that said diffused power density does not induce decomposition of tissue other than at the cataracted lens tissue, and
(d) scanning the cataracted lens tissue with said focal spot and within a predetermined limiting perimeter until ablative photodecomposition and/or thermal decomposition and/or photofragmentation and/or photoemulsification is substantially complete within said perimeter.

17. The method of claim 16, in which the iris of the eye is dilated and said perimeter is within the inner confines of the dilated iris.

18. The method of claim 16, in which the convergent ray bundle has an included angle in the range of about 15 to about 30 degrees at entrance to the cornea of the eye.

19. The method of claim 16, in which first scanning is limited to a first and relatively small central area within said perimeter, and in which the focal spot is successively advanced in increments of depth into the lens tissue for each succeeding scan of a progressively larger centered area within said perimeter.

20. The method of claim 19, in which, after progressively larger scans have reached a scan of the area bounded by said perimeter, the focal spot is successively advanced in increments of depth into the lens tissue for each succeeding scan of a progressively smaller centered area within said perimeter.

21. The method of claim 16, in which an irrigation/aspiration procedure is performed with an isotonic solution in the anterior chamber of the eye throughout the period of laser excitation.

22. The method according to claim 16, in which the laser is of a variety characterized by emission in the ultraviolet.

23. The method according to claim 22, in which the laser is an excimer laser.

* * * * *